US012427290B2

(12) United States Patent
Gomes et al.

(10) Patent No.: US 12,427,290 B2
(45) Date of Patent: Sep. 30, 2025

(54) PERFUSION BALLOON WITH INTERNAL VALVE

(71) Applicant: C.R. Bard, Inc., Franklin Lakes, NJ (US)

(72) Inventors: Garrett Gomes, San Mateo, CA (US); Andrew Moll, Burlingame, CA (US); Cameron Moore, Fremont, CA (US); Samuel Radochonski, San Francisco, CA (US); Chander Virk, Redwood City, CA (US); Anthony Young, San Jose, CA (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 143 days.

(21) Appl. No.: 18/102,822

(22) Filed: Jan. 30, 2023

(65) Prior Publication Data

US 2023/0330397 A1    Oct. 19, 2023

Related U.S. Application Data

(63) Continuation of application No. 15/061,719, filed on Mar. 4, 2016, now Pat. No. 11,565,090.

(51) Int. Cl.
*A61M 25/10* (2013.01)
*A61M 25/00* (2006.01)
*A61M 29/02* (2006.01)

(52) U.S. Cl.
CPC .. *A61M 25/10185* (2013.11); *A61M 25/1002* (2013.01); *A61M 29/02* (2013.01);
(Continued)

(58) Field of Classification Search
CPC ............ A61M 1/3613; A61M 25/0075; A61M 25/1002; A61M 2005/1406;
(Continued)

(56) References Cited

U.S. PATENT DOCUMENTS 5,360,403 A * 11/1994 Mische ................. A61M 25/10
604/101.02
6,045,531 A * 4/2000 Davis ................ A61M 25/0075
604/101.05
(Continued)

FOREIGN PATENT DOCUMENTS

EP        2438882 A1     4/2012
KR     1020140039164 A    4/2014
KR     1020150017345 A    2/2015

*Primary Examiner* — Elizabeth Houston
*Assistant Examiner* — Lindsey Bachman
(74) *Attorney, Agent, or Firm* — Dickinson Wright PLLC; Andrew D. Dorisio; Nicholas P. Coleman

(57) ABSTRACT

An apparatus for performing a medical procedure and, in particular, an aortic valvuloplasty, in a vessel for transmitting a flow of fluid. The apparatus comprises a shaft, an inflatable perfusion balloon supported by the shaft and including an internal passage for permitting the fluid flow in the vessel while the perfusion balloon is in an inflated condition, and a valve for controlling the fluid flow within the passage. The valve may be connected to the shaft, or may comprise an elongated tube partially connected to the balloon. The balloon may comprise a plurality of cells in a single cross-section, each cell including a neck, and the valve may be positioned in a space between the shaft and the necks for controlling the fluid flow within the passage. A connector may also be provided to control the position of the valve.

15 Claims, 8 Drawing Sheets

(52) U.S. Cl.
CPC ............ *A61M 2025/0076* (2013.01); *A61M 2025/1072* (2013.01); *A61M 2025/1081* (2013.01); *A61M 2025/1097* (2013.01); *A61M 2210/125* (2013.01)

(58) Field of Classification Search
CPC .. A61M 2025/0076; A61M 2025/0078; A61M 2025/1095; A61M 2025/1097
See application file for complete search history.

(56) References Cited

U.S. PATENT DOCUMENTS

| | | |
|---|---|---|
| 7,708,753 B2 | 5/2010 | Hardert |
| 7,951,111 B2 * | 5/2011 | Drasler ............. A61M 25/1002 604/100.01 |
| 2008/0228139 A1 | 9/2008 | Melsheimer et al. |
| 2009/0118681 A1 * | 5/2009 | Molgaard-Nielsen ....................... A61M 39/228 604/246 |
| 2009/0264820 A1 * | 10/2009 | Kung .................... A61F 2/2433 604/99.04 |
| 2011/0264039 A1 * | 10/2011 | Thielen .............. A61B 17/2202 606/192 |
| 2014/0066896 A1 | 3/2014 | Tilson |
| 2015/0272732 A1 | 10/2015 | Tilson |

\* cited by examiner

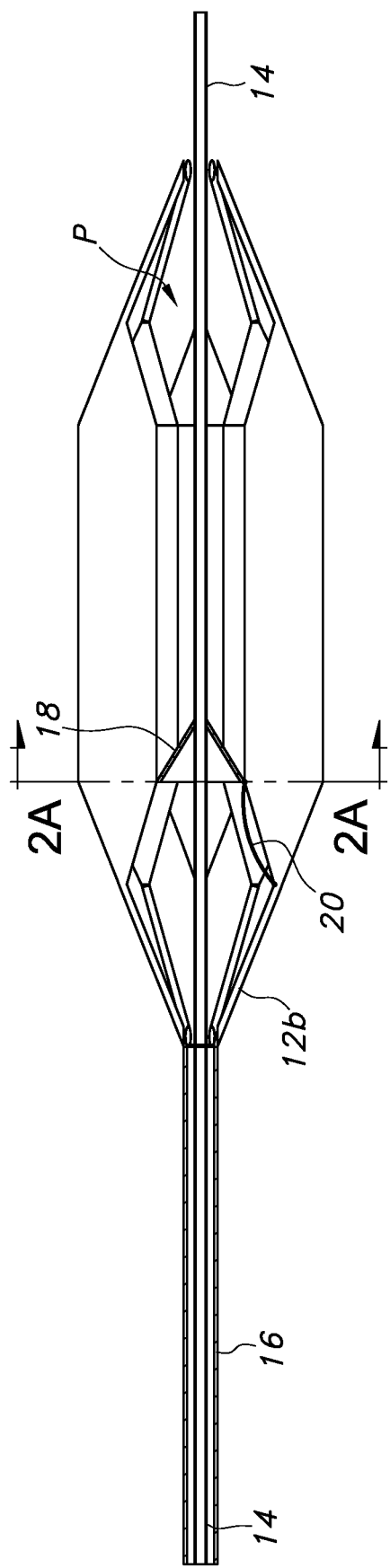
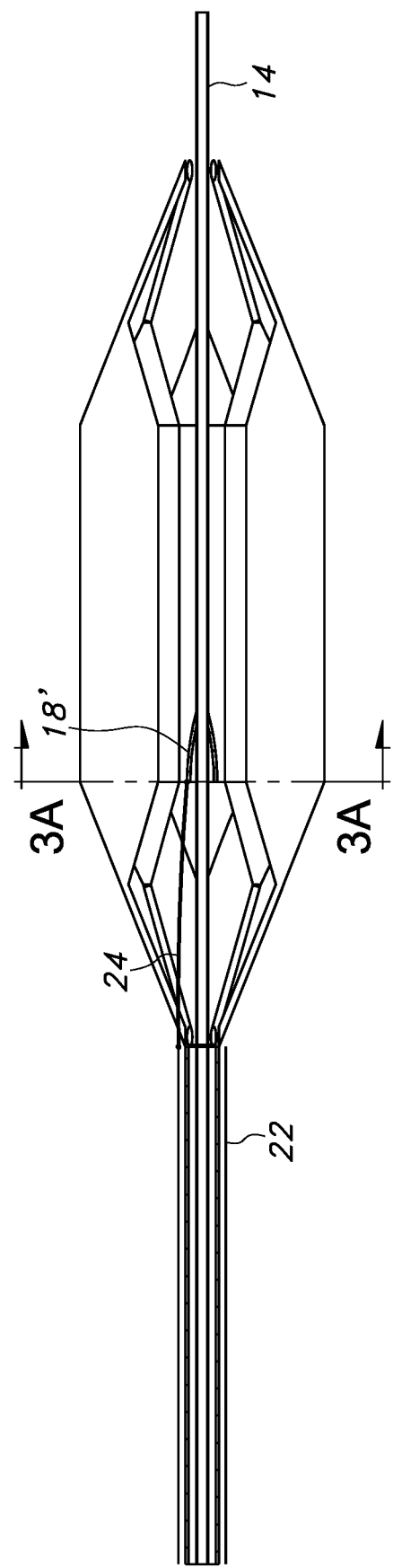

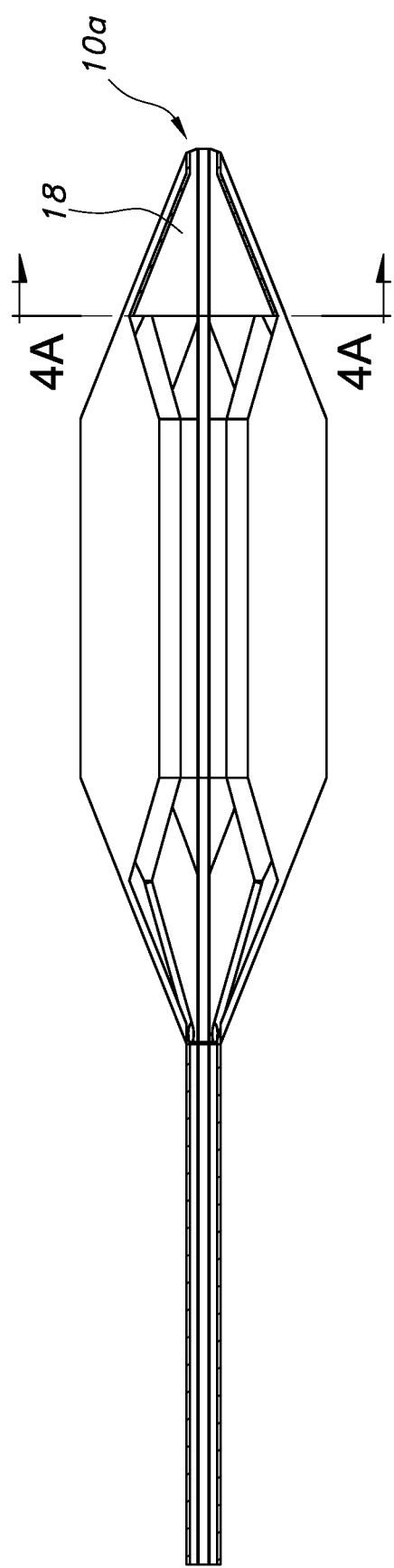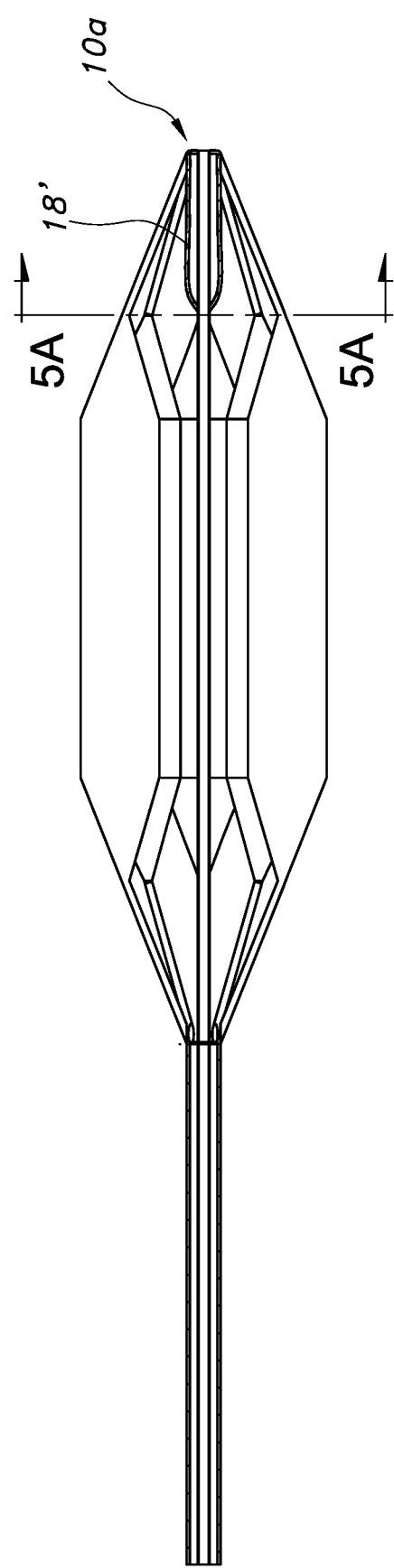
FIG. 4
FIG. 5

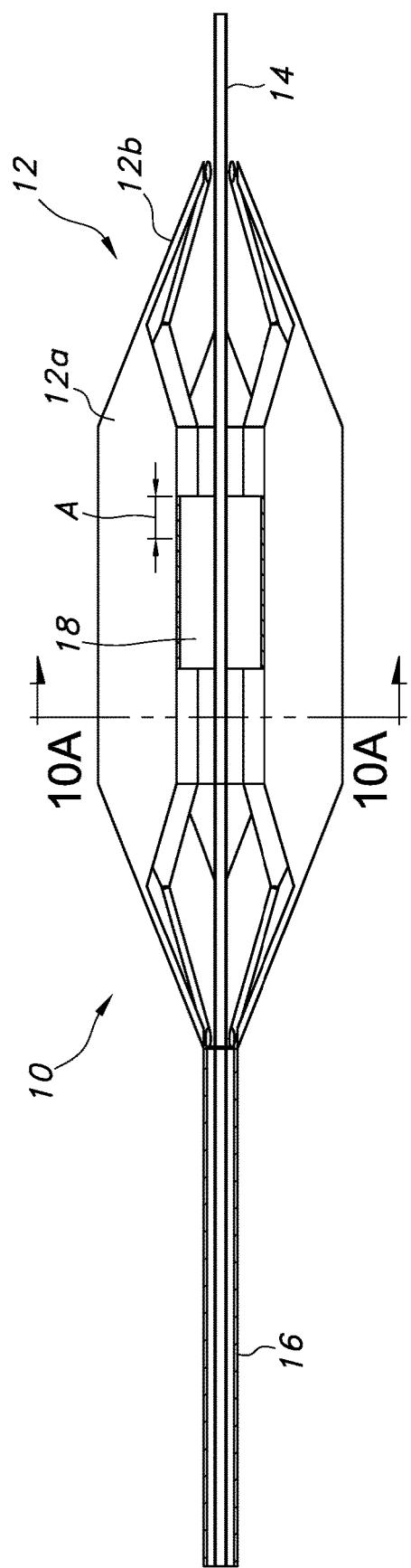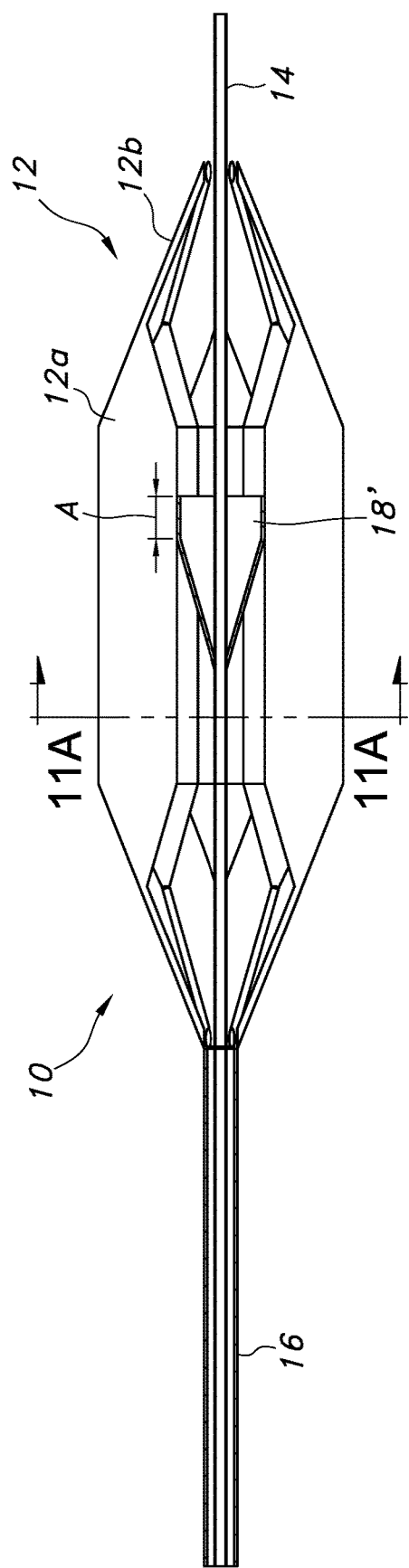

PERFUSION BALLOON WITH INTERNAL VALVE

INCORPORATION BY REFERENCE

This application is a continuation of U.S. application Ser. No. 15/061,719 filed on Mar. 4, 2016, the disclosure of which is hereby incorporated by reference.

BACKGROUND

Expandable devices, such as balloons, are widely used in medical procedures. In the case of a balloon, it is inserted in a body, typically on the end of a catheter, until the balloon reaches the area of interest. Adding pressure to the balloon causes the balloon to inflate. In one variation of use, the balloon creates a space inside the body when inflated.

Balloons may be used in the valves associated with the heart, including during Balloon Aortic Valvuloplasty (BAV) (as described in Hara et al. "Percutaneous balloon aortic valvuloplasty revisited: time for a renaissance?" *Circulation* 2007; 115:e334-8) and Transcatheter Aortic Valve Implantation (TAVI)). For such a procedure, the inflated balloon may be designed to allow for continued blood flow, or perfusion. However, when the balloon is inflated, the heart valve is necessarily temporarily disabled. This can lead to disruptions in the blood flow, including by creating undesirable back flow.

Thus, it would be desirable to provide a perfusion balloon that can be used to regulate the flow of fluid during a procedure, especially when used in connection with a procedure involving a valve that is disabled as a result of the procedure or otherwise.

SUMMARY OF THE DISCLOSURE

The technical effect of the disclosed embodiments may be considered to include achieving valving internal to a perfusion balloon, which creates an enhanced flow of fluid during the opening of the valve, enhanced blocking of the flow during the closing of the valve, and/or creates an easier manner to manufacture the balloon including the valve.

According to one aspect of the disclosure, an apparatus for performing a medical procedure in a vessel for transmitting a flow of fluid includes a shaft and an inflatable perfusion balloon supported by the shaft. The balloon includes an internal passage for permitting the fluid flow in the vessel while the perfusion balloon is in an inflated condition, and a valve connected to the shaft for controlling the fluid flow within the passage.

In one embodiment, the valve comprises a body having a generally frusto-conical shape in an expanded condition. The valve may comprise a single body, and may comprise one or more flaps. The valve may further include an aperture for receiving a portion of the balloon.

The balloon may comprise a plurality of cells in a single cross-section bounding the internal passage, and the valve may be positioned in a portion of the internal passage formed by the cells. Each cell may comprise a neck, and the valve is located in a space between the necks and the shaft. The valve may be connected to at least one of the necks.

The apparatus may further include a connector for connecting the valve to the balloon. The connector may be provided for connecting the valve to the balloon, the shaft or an associated sheath. The connector may comprise a tether in the form of a wire, fiber, ribbon, or like flexible structure.

Another aspect of the disclosure pertains to an apparatus for performing a medical procedure in a vessel for transmitting a flow of fluid. The apparatus includes a shaft and an inflatable perfusion balloon supported by the shaft. The balloon includes an internal passage for permitting the fluid flow in the vessel while the perfusion balloon is in an inflated condition. An elongated tube is adapted for partially collapsing to control the fluid flow within the passage, thereby forming a valve.

In one embodiment, the tube is at least partially connected to the balloon. The tube may include a distal portion connected to the balloon and a proximal portion not connected to the balloon. The proximal portion may have a continuous cross-section forming a full or at least partial circumferential seal with the balloon.

The balloon may comprise a plurality of cells in a single cross-section, and the tube is positioned in a part of the passage formed by the plurality of cells. Each of the cells may be rounded along an inner face At least a portion of the tube connected to the cells may comprise a cross-section in the form of a star having projections for positioning between adjacent cells and recesses between the projections for engaging the rounded cells.

Still a further aspect of the disclosure pertains to an apparatus for performing a medical procedure in a vessel for transmitting a flow of fluid. The apparatus comprises a shaft and an inflatable perfusion balloon supported by the shaft. The balloon includes an internal passage for permitting the fluid flow in the vessel while the perfusion balloon is in an inflated condition. The balloon includes a generally tapered portion extending toward the shaft. A valve is positioned in a space between the shaft and the balloon in the generally tapered portion for controlling the fluid flow within the passage.

In one embodiment, the valve comprises a body having a generally frusto-conical shape in an expanded condition. The valve may comprise a single body, or may comprise a plurality of flaps. The valve may include an aperture for receiving a portion of the balloon. The generally tapered portion for receiving the valve may be located at a distal end portion of the balloon, but could be located at the proximal end as well.

In yet another aspect, the disclosure pertains to an apparatus for performing a medical procedure in a vessel for transmitting a flow of fluid. The apparatus comprises a shaft and an inflatable perfusion balloon supported by the shaft. The balloon includes an internal passage for permitting the fluid flow in the vessel while the perfusion balloon is in an inflated condition, a valve for controlling the fluid flow within the passage, and a connector for connecting to the valve to control the position thereof.

In one embodiment, the connector comprises a tether extending between the valve and the balloon for preventing the valve from inverting. The connector may comprise a tether extending between the valve and the shaft or an associated sheath. The tether may comprise a wire, fiber, ribbon, or like flexible structure.

BRIEF DESCRIPTION OF THE DRAWINGS

FIG. 2 is a cross-sectional side view of the device of FIG. 1 along line 2-2, with a valve in a first position for restricting flow through a central passage of the device;

FIG. 3 is a cross-sectional side view of the device of FIG. 1, with the valve in a second position for permitting flow through a central passage of the device;

FIG. 4 is a cross-sectional side view of another embodiment of an inflatable device including a valve in a first position for blocking flow through a central passage of the device;

FIG. 5 is a cross-sectional side view of the device of FIG. 4, with the valve in a second position for permitting flow through a central passage of the device;

FIG. 10 is a cross-sectional side view of another embodiment of an inflatable device including a valve in a first position for permitting flow through a central passage of the device;

FIG. 11 is a cross-sectional side view of the device of FIG. 10, with the valve in a second position for permitting flow through a central passage of the device.

DETAILED DESCRIPTION

The invention disclosed pertains to an inflatable device in the nature of a perfusion balloon. The novel features of the invention are set forth with particularity in the claims that follow. A better understanding of the features and advantages of the invention will be obtained by reference to the following detailed description that sets forth illustrative embodiments, in which the principles of the invention are utilized, and the accompanying drawings.

Figure 1:
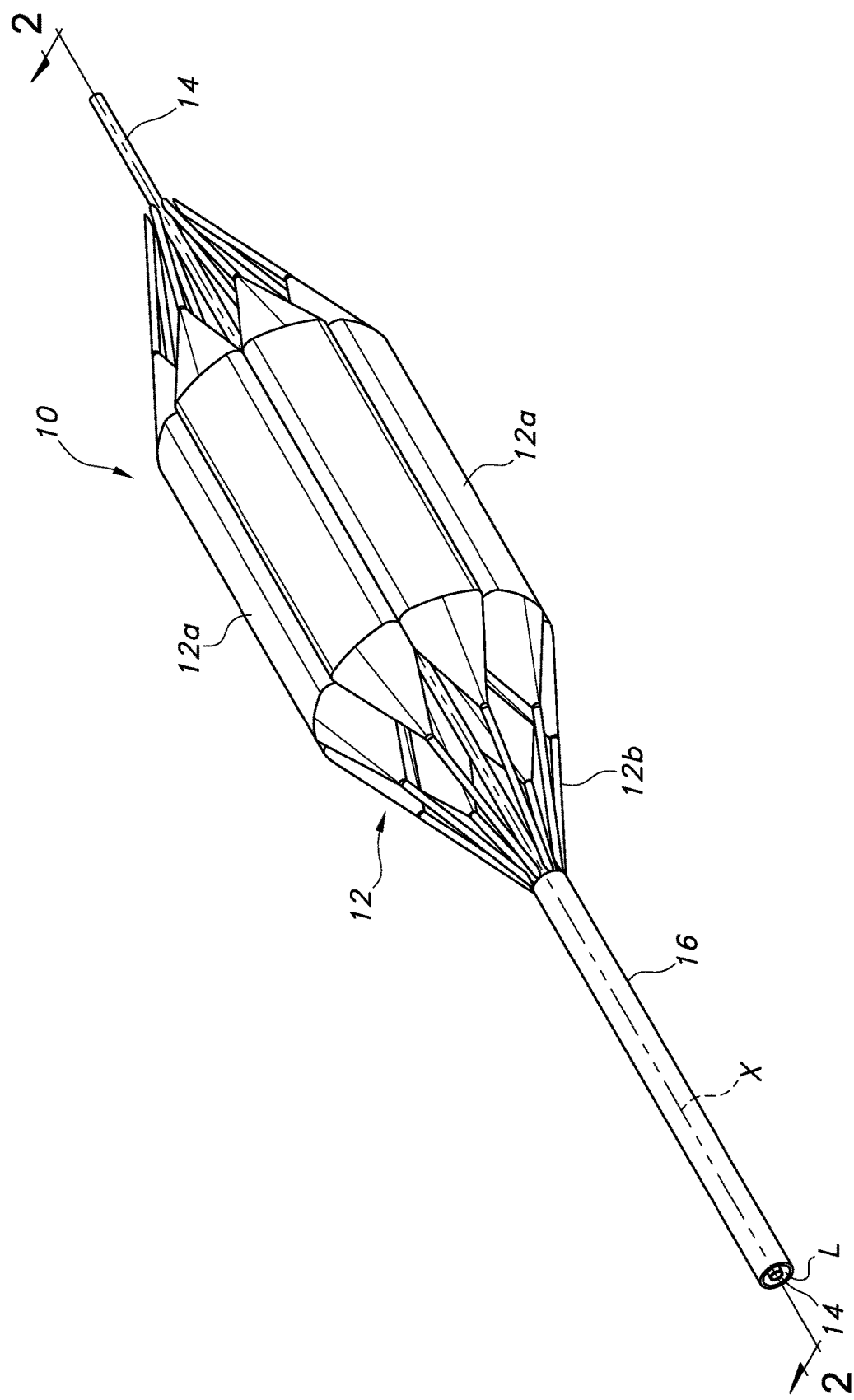
FIG. 1 is a perspective view of an inflatable device in the expanded condition.
Figure 3A:
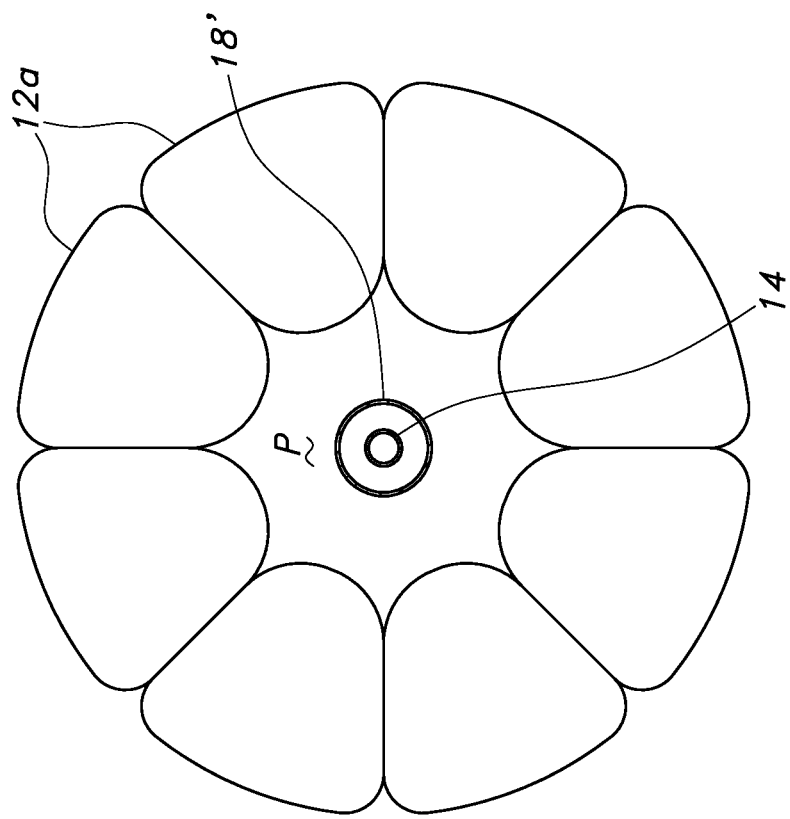
FIG. 3A is a cross-sectional view taken along line 3A-3A of FIG. 2.
Figure 2A:
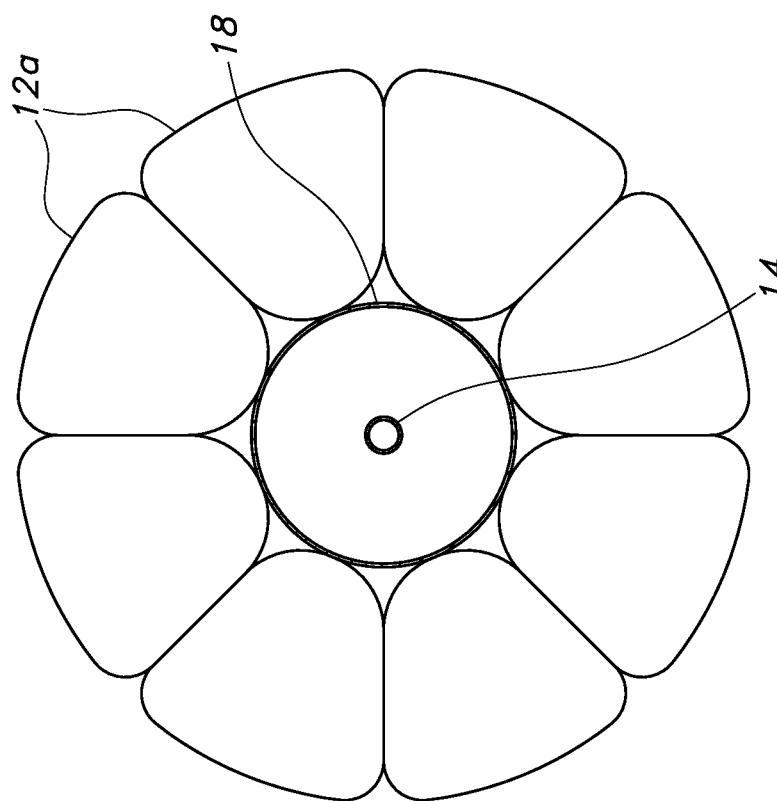
FIG. 2A is a cross-sectional view along line 2A-2A of FIG. 2.

FIG. 1 shows an inflatable device 10 including a perfusion balloon 12 in an inflated condition, ready for use in connection with a procedure (but which balloon would normally be folded for purposes of delivery through the vasculature to a selected treatment area, such as the aortic valve). From viewing the inflated condition, it can be understood that the balloon 12 of the device 10 may have multiple inflatable cells 12a (eight shown, but any number may be provided) in at least a single cross-section of the balloon (see, e.g., FIGS. 2A and 3A). A retainer, such as a tubular, flexible sheath or covering (not shown for purposes of clarity), may be provided over the central portion of the cells 12a to retain them in a generally annular configuration in the illustrated embodiment, and may also serve to protect the cells when contact is made with a stenosed valve or the like. The sheath or covering may be made non-compliant, such that inflation of the cells 12a expands the covering to engage an external structure, such as a valve forming part of the vasculature or other structure in a body.

The cells 12a may be individual or discrete, separately inflatable balloons. Each cell 12a having a separate inflation lumen via neck 12b, as noted, and also a neck 12c at the distal end, which form generally tapered portions of the balloon 12. The cells 12a may be sealed at a distal tip (such as at the distal end of each neck 12c), or may be parts of a single balloon. The latter may be achieved by a segmented, elongated structure that is folded in a manner that causes the cells 12a to form a passage P extending along a central axis X, along which fluid such as blood may continue to flow, even when the balloon 12 is fully inflated (which may be done through a single inflation lumen, or each balloon could have its own inflation lumen). A full description of this type of balloon may be found in International Patent Application Publication No. WO2012099979A1. However, other forms of perfusion balloons could also be used, such as for example a tubular balloon, one having a peripheral (e.g., helical) channel for purposes of allowing fluid flow to occur during inflation, or any combination of these technologies.

In any case, the device 10 may also include an inner shaft or tube 14 including a lumen L extending along the central axis X, which may be adapted for receiving a guidewire for guiding the device to a treatment location. The inner tube 14 may form part of a catheter shaft or tube 16, which includes a lumen N in which the inner tube 14 is positioned. The perfusion balloon 12 may in turn be supported by and attached to the catheter shaft 16, such as at the proximal necks 12b forming the entrance to passage P, which may receive inflation fluid through the lumen N.

According to one aspect of the disclosure, the balloon 12 is adapted for selectively regulating the flow of fluid through the passage P. In one embodiment, this is achieved using a valve 18 comprising a selectively actuated body that, when actuated for occupying the passage P (FIG. 2A) such as the result of fluid flow in one direction (such as caused during diastole), substantially blocks it and thus retards or prevents fluid flow. When unactuated (folded down or collapsed; see valve 18' in FIGS. 3, 3A), such as during systole, the valve 18 allows substantial flow through the passage P. The valve 18 may thus repeatedly and regularly restrict and allow fluid flow through the passage P when the balloon 12 is inflated, such as in the space including the aortic valve, and thus mimics the function of the otherwise disabled valve.

In the illustrated embodiment, the valve 18 comprises a single piece of a flexible material having a generally frusto-conical shape. However, the valve may take other forms, including as outlined further in the following description. In some embodiments, the valve 18 comprises a plurality of pieces of material, which may be separate or connected.

The valve 18 may be positioned anywhere within the passage P, such as adjacent to the open proximal end of it with the larger open end of the cone facing proximally. However, the valve 18 could alternatively be located at the distal end of the device 10. The valve 18 may also be reoriented to open facing distally, if used transapically. Regardless of the particular position or orientation, the valve 18 is arranged to provide a one way valve function during a procedure using the device 10.

In one embodiment, the material forming the valve 18 is connected at the innermost portion to the shaft or tube 14 passing through the balloon 12. Thus, as can be understood from FIG. 2A, when of a frusto-conical shape, the material forming the valve 18 includes an opening 18a for receiving the shaft or tube 14. The connection may be established by known bonding methods, such as adhesives, tapes, welding, or the like. The material forming the valve 18 may be otherwise substantially continuous, or could be provided in two or more segments in order to achieve a desired valving function (e.g., two segments to simulate a bicuspid valve, three to simulate a tricuspid, etc.) depending on the particular use. Alternatively, the valve 18 may be provided so as to be slidably connected to the tube 14, such that it may move to and fro therealong to regulate flow.

Along the periphery of the valve 18, the material is not connected to the interior of the balloon 12 (e.g. cells 12a). This will allow the valve to collapse and permit the fluid flow through passage P. However, it is possible to connect part of the periphery of the material forming the valve 18 to the balloon 12, such as to one or more of the cells 12a or perhaps even the necks 12b, to allow for the valve 18 to only partially collapse. Adjustments can be made in this manner to provide a desired regulation of the fluid flow.

As shown in FIG. 2, the valve 18 may also be connected to the device 10 by an optional connector 20. The connector 20 may extend between the periphery of the valve 18 and the balloon 12, such as at the junction between one cell 12a and the corresponding neck 12b. This connector 20 serves as a tether that prevents the valve 18 from inverting in the passage 18, but is sufficiently sized so as to not prevent the desired movement between the actuated and non-actuated conditions. The connector 20 may comprise a ribbon, wire, fiber, or like structure having sufficient flexibility to achieve the desired function.

The valve 18 may also be connected to a structure external to the balloon 12, such as a sheath 22 or the shaft 16, for controlling the position of the valve 18. This can be done using a connector 24, similar to connector 20, which thus forms a tether. This allows for the valve 18 to be forcibly collapsed by retracting the tube 16 or sheath 22. This may be done to ensure that removal of the device 10 may be reliably achieved without interference from valve in the actuated or expanded condition.

Figure 5A:
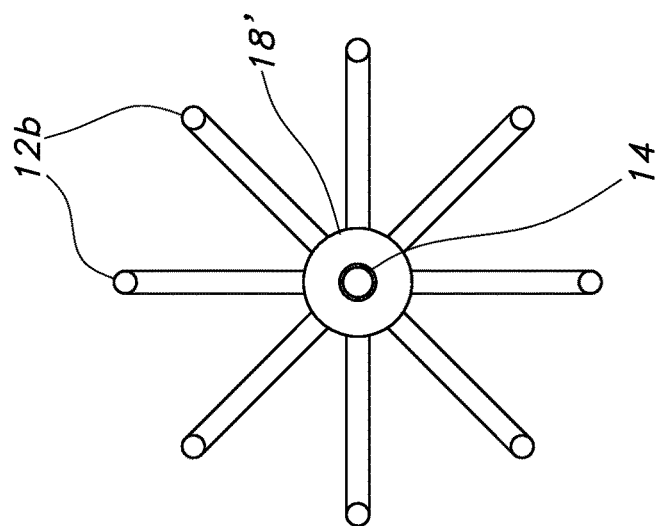
FIG. 5A is a cross-sectional view taken along line 5A-5A of FIG. 5.
Figure 4B:
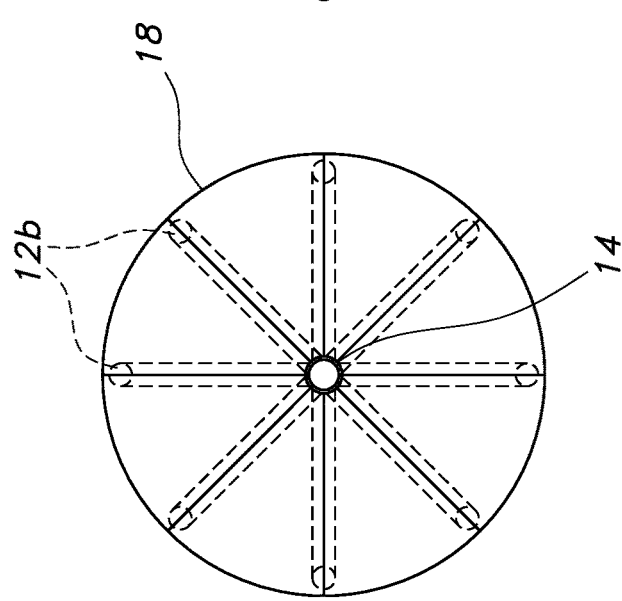
FIG. 4B is a cross-sectional view similar to FIG. 4A showing an alternate embodiment.
Figure 4A:
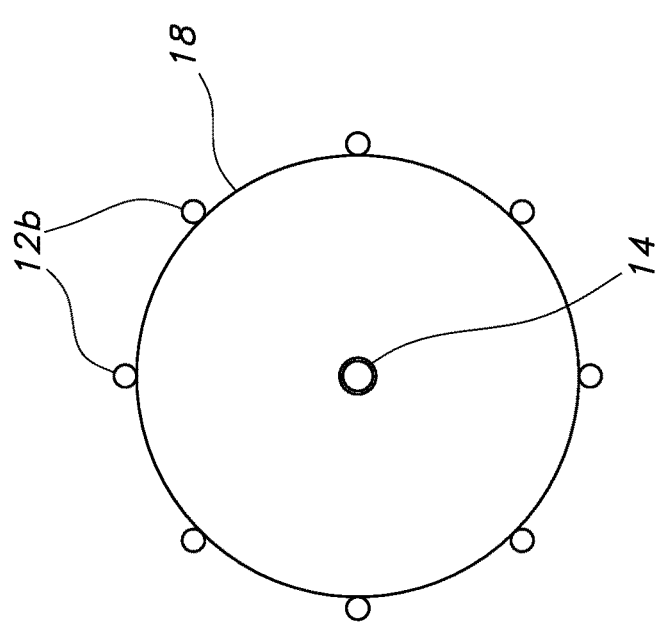
FIG. 4A is a cross-sectional view along line 4A-4A of FIG. 4.

Reference is now made to FIGS. 4 and 5, which illustrate a further embodiment of a possible valving arrangement for a perfusion balloon, such as the multi-cellular balloon 12 illustrated. In this embodiment, the valve 18 is formed of a body comprised of a flexible material in a generally frusto-conical shape when actuated (FIGS. 4 and 4A) to restrict flow through passage P, and then collapsed to permit substantially unrestricted flow (FIGS. 5 and 5A). However, as can be appreciated, the valve 18 in this embodiment is located at the distal end of the balloon 12 within the distal necks 12c of the balloon cells 12a. More specifically, the valve 18 is located in an internal space between the tube 14 and a cage formed by the necks 12c. The valve 18 could also be positioned at the proximal end of the balloon, such as in a similar location.

Again, the valve 18 may be formed as a single body (e.g., of a single piece of material), or may be formed as a series of flaps (such as, for example, eight flaps 18a-18g, as indicated in FIG. 4B). In any case, the material may be connected along the inner portion to the tube 14, such as by bonding (adhesive, welding (thermal or otherwise), tape, etc.). Alternatively or additionally, the material forming valve 18 may be bonded to form part of the distal tip 10a of the device 10.

Figure 6:
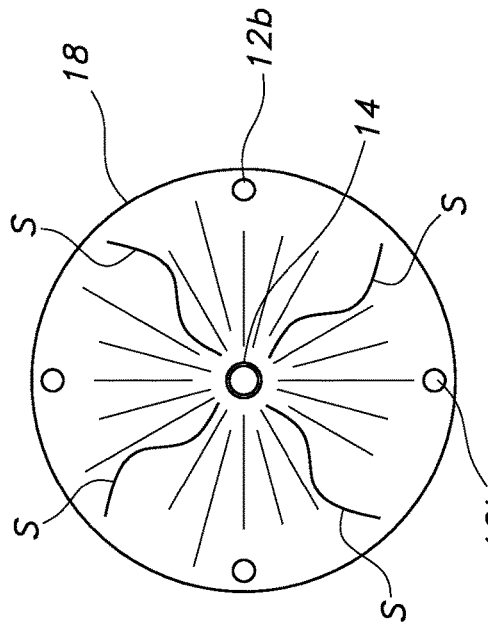
FIGS. 6-9 are cross-sectional views similar to FIG. 4A illustrating different embodiments of valves.

The material forming valve 18 may also be optionally connected to the balloon 12, such as along one or more of the necks 12c, and for erecting in a space between the necks and the shaft 14 internal to the balloon. The connection may be established using bonds, such as by welding or adhesives (glue, tape, etc.), or by way of a mechanical connection. In one particular embodiment, the material forming the valve 18 is provided with one or more apertures, each for receiving a neck 12c of one of the balloon cells 12a or other structures connected to the balloon 12. Thus, as shown in FIG. 6, which is a similar view to FIG. 4A, the necks 12c may serve to support the valve 18 in a manner that allows it to at least partially collapse.

Figure 7:
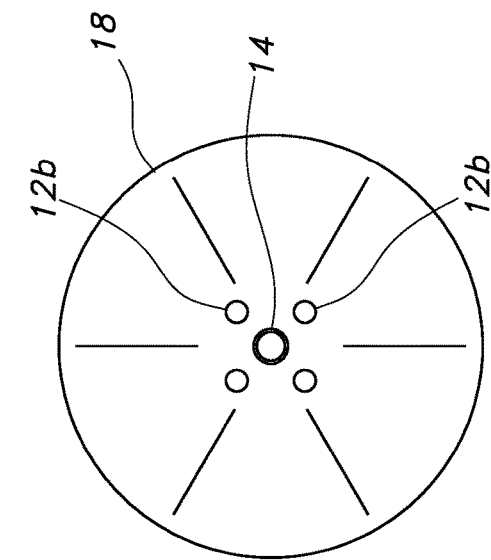

In this or other embodiments, the valve 18 material may also be provided with one or more slits S (see FIG. 7) for selectively blocking and allowing fluid flow based on the relative flexing or bulging of the material forming the body of the valve caused by the resulting changes in fluid flow and pressure during systole and diastole. The slits S may extend radially, as shown, or may extend circumferentially, but other orientations are possible as well.

Figure 8:
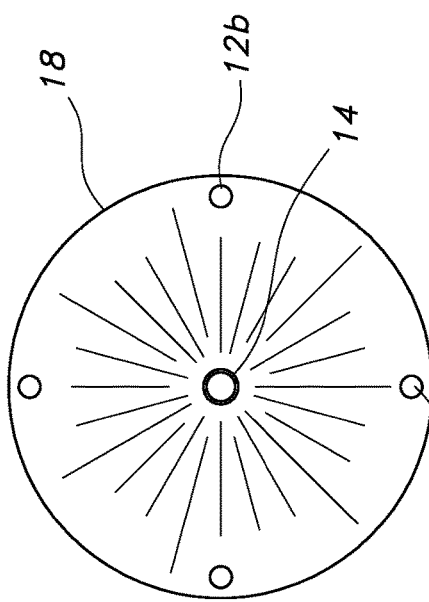
Figure 9:
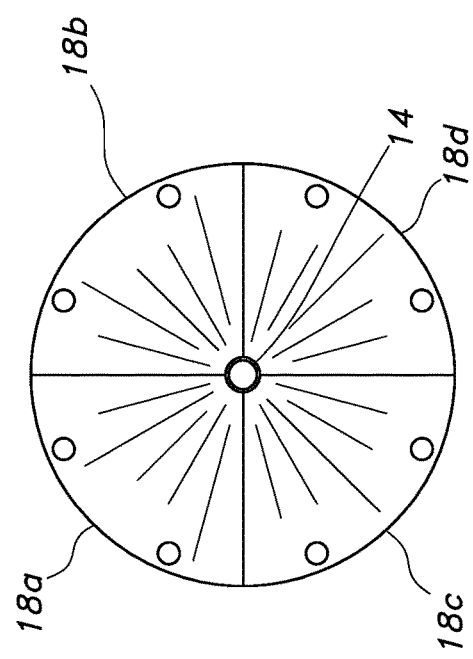

As noted previously, the material forming the body of the valve 18 may also be separated or divided into parts (note four quarters 18a-18d in FIG. 8), each associated with one or more of the necks 12c along the periphery and partially or fully bonded to the tube 14 or tip 10a at the inner portion. The mechanical connection with the neck(s) 12c may additionally or alternatively be provided along the inner portion of the material forming valve 18 in any of these embodiments, as indicated in FIG. 9, in which case a connection with the tube 14 may be optional.

In the above situations where there is a mechanical connection established, it can be appreciated that the necks 12c may help to erect the valve 18 to the operative condition when the balloon 18 is inflated, and further aid in collapsing it when deflated. In any case, the material forming the valve 18 may also be provided with properties to facilitate preferential folding when the balloon 12 is collapsed, and then expansion. This may be achieved, for example, by the use of different thickness of material to create living hinges or like structures that cause the material to fold or otherwise behave in a certain manner. The material of the valve body may also be provided with fold lines, pleats, beads, or supports to cause folding and unfolding to occur in a preferential manner to ensure that the valve 18 expands or collapses in the intended way to achieve the desired valving function.

The valve 18 may also take shapes other than fruso-conical. For example, FIGS. 10-11 illustrate a valve 18 having a body in the form of a generally cylindrical tube positioned in the passage P. The tube may be made of a film adhered at least partially to the interior of the balloon 12, such as along the surfaces of cells 12a forming the passage P, but could also be located at other portions of the balloon, such as along the tapered sections formed by necks 12b, 12c. Specifically, a first portion of the tube (which may be distally located) having a continuous cross-section may be adhered to the balloon 12, such as along portion A, while a second portion (which may be proximally located, and may also have a continuous cross-section) remains unattached to the balloon. The attachment may be achieved using bonding, such as adhesives (glue, epoxy, etc.), tape, welding, or other forms of thermal adhesion, etc., such that a circumferential seal is formed along the periphery of the valve 18. Alternatively, the sealing may be such that only parts of the tube are adhered (such as to achieve collapsing in a manner that replicates the function of a bi-cuspid, tri-cuspid, or other desired form of collapsing, depending on the circumstances), with the understanding that aortic regurgitation may result when used in connection with the aortic valve. Again, if the tube 18 is positioned elsewhere, then the location of the attachment, such as portion A, would be repositioned accordingly (such as along necks 12b, 12c, with a discontinuous seal thus being formed).

Figure 11A:
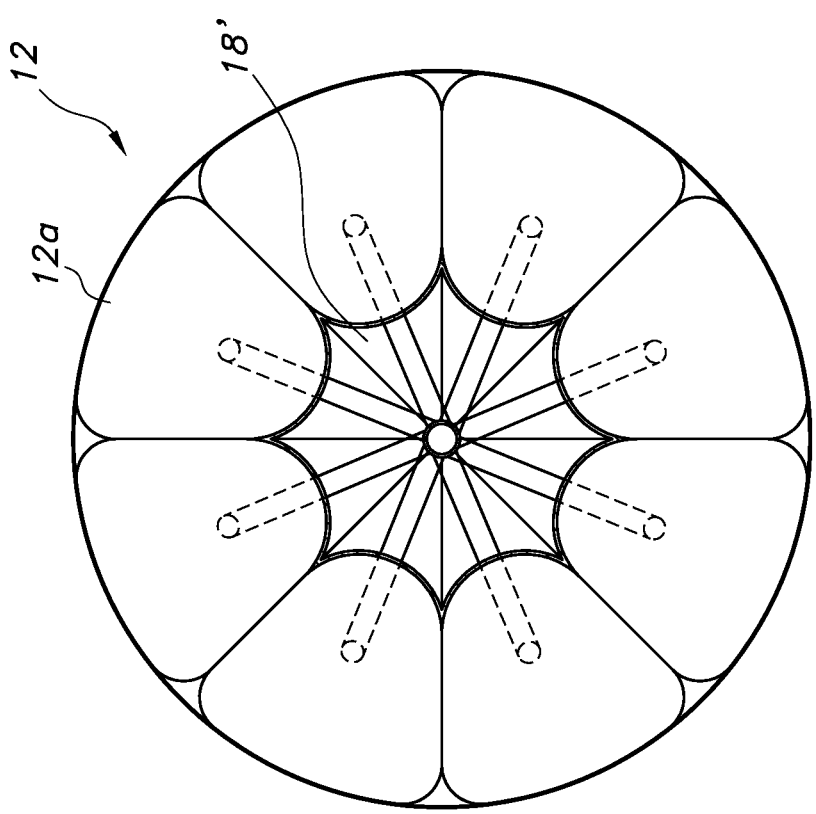
FIG. 11A is a cross-sectional view along line 11A-11A of FIG. 11.
Figure 10A:
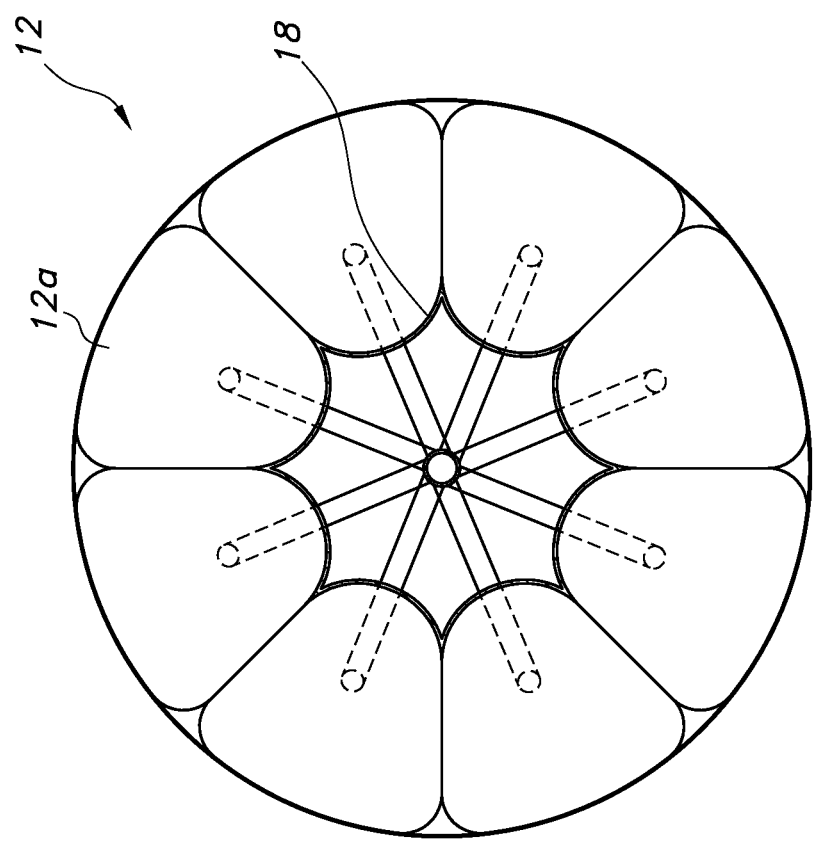
FIG. 10A is a cross-sectional view along line 10A-10A of FIG. 10.

Consequently, when fluid flows through the passage in the proximal direction, the valve 18 remains open, as shown in FIGS. 10 and 10A. When the flow direction is reversed, the resulting negative pressure created may cause the unattached portion of the tube forming the valve 18 to collapse over the tube 14, as shown in FIGS. 11 and 11A, and thus hinder the flow of fluid through the passage P in the opposite direction.

A one way valve is thus formed in a passive manner. Again, the orientation may be reversed depending on the particular use, and the positioning may be such that the unattached portion is not within the portion of the passage P bounded by cells 12a, but rather by necks 12b, 12c.

The valve 18 in this embodiment may be positioned anywhere along the passage P, and the overall length may be adjusted to achieve different performance characteristics (with a shorter length requiring less material and thus leading to enhanced trackability and sheath compatibility). To achieve the desired sealing along portion A, the tube forming the valve 18 may have an eight-sided star shape in cross-section (see FIG. 11A). In the case where each of the cells 12a has a rounded inner face, the valve 18 may have projections for positioning between adjacent cells and recesses between the projections for engaging the rounded cells. However, the valve 18 could also have a cross-section that is circular, square, rectangular, oval, triangular, or any other shape depending on the configuration of perfusion balloon 12. The cross-section may also be continuous, tapered, stepped, or discontinuous. The orientation of the valve 18 may also be reversed for a transapical procedure.

Various materials may be used for forming the described structures, including as outlined in International Patent Application Publication No. WO2012099979A1.

The foregoing discussion is intended to provide an illustration of the inventive concepts, and is not intended to limit the invention to any particular mode or form. Any elements described herein as singular can be pluralized (i.e., anything described as "one" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. Terms like "generally" or "substantially" mean that the value may vary depending on the circumstances, such as up to 10% of a given condition. The above-described configurations, elements or complete assemblies and methods and their elements for carrying out the invention, and variations of aspects of the invention can be combined and modified with each other in any combination, along with any obvious modifications.

The invention claimed is:

1. An apparatus for performing a medical procedure in a vessel for transmitting a flow of fluid and in connection with an inflation fluid, comprising:
    a shaft including a first lumen for receiving a guidewire, the first lumen having an inlet and an outlet, and a second lumen for receiving the inflation fluid;
    an inflatable perfusion balloon supported by the shaft and adapted for receiving the inflation fluid from the second inflation lumen of the shaft to achieve an inflated balloon condition, the inflatable perfusion balloon including an internal passage for permitting the fluid flow in the vessel when the perfusion balloon is in an inflated condition; and
    a valve attached to an external surface of the shaft within the internal passage, said valve adapted for extending radially outward from the external surface for controlling the fluid flow in the internal passage;
    wherein the internal passage is exterior to the shaft and is formed at least partially by a wall of the inflatable perfusion balloon.

2. The apparatus of claim 1, wherein the valve comprises a body having a generally frusto-conical shape in an expanded condition.

3. The apparatus of claim 1, wherein the valve comprises a single body or a plurality of flaps.

4. The apparatus of claim 1, wherein the balloon comprises a plurality of cells in a single cross-section bounding the internal passage, at least one cell of the plurality of cells including an inner surface opposing an outer surface of the shaft, the valve being positioned in a portion of the internal passage formed by the cells.

5. The apparatus of claim 1, further including a connector for connecting the valve to the balloon, the shaft or a sheath associated with the shaft.

6. The apparatus of claim 1, wherein the first lumen extends at least partially through the valve.

7. An apparatus for performing a medical procedure in a vessel for transmitting a flow of fluid and in connection with an inflation fluid, comprising:
    a shaft having an outer surface, the shaft including a lumen for receiving a guidewire;
    an inflatable perfusion balloon supported by the shaft and adapted for receiving the inflation fluid to achieve an inflated condition, the balloon including an internal passage at least partially formed by an inner surface of the balloon and an outer surface of the shaft for permitting the fluid flow in the vessel when the perfusion balloon is in an inflated condition; and
    a valve attached to the outer surface of the shaft within the internal passage, the valve adapted for expanding radially outward from the outer surface for controlling the fluid flow in the internal passage.

8. The apparatus of claim 7, wherein the valve comprises a body having a generally frusto-conical shape in an expanded condition.

9. The apparatus of claim 7, wherein the valve comprises a single body or a plurality of flaps.

10. The apparatus of claim 7, wherein the balloon comprises a plurality of cells in a single cross-section bounding the internal passage, and the valve is positioned in a portion of the internal passage formed by the cells.

11. The apparatus of claim 7, further including a connector for connecting the valve to the balloon, the shaft or a sheath associated with the shaft.

12. The apparatus of claim 7, wherein the valve comprises a selectively actuatable valve adapted to be selectively actuated between a deployed and a non-deployed position when the perfusion balloon is in the inflated condition.

13. An apparatus for performing a medical procedure in a vessel for transmitting a flow of fluid and in connection with an inflation fluid, comprising:
    a shaft having an outer surface, the shaft including a lumen for receiving a guidewire;
    an inflatable perfusion balloon supported by the shaft and adapted for receiving the inflation fluid to achieve an inflated condition, the balloon including an internal passage between an inner surface of the balloon and an outer surface of the shaft for permitting the fluid flow in the vessel when the perfusion balloon is in an inflated condition; and
    a valve attached to the outer surface of the shaft and extending radially outwardly toward the inner surface of the inflatable perfusion balloon for controlling the fluid flow within the internal passage.

14. The apparatus of claim 13, wherein the valve comprises a body having a generally frusto-conical shape in an expanded condition.

15. The apparatus of claim 13, wherein the valve comprises a plurality of flaps.

\* \* \* \* \*